United States Patent
Stebbins et al.

(10) Patent No.: US 12,208,154 B2
(45) Date of Patent: Jan. 28, 2025

(54) FATTY-OIL-FREE, LOW-FRICTION CLEANSER WITH HIGH-FOAMING PROPERTIES

(71) Applicant: L'OREAL, Paris (FR)

(72) Inventors: Nicholas David Stebbins, Clark, NJ (US); Susan Halpern Chirch, Basking Ridge, NJ (US); Ryuji Hara, Westfield, NJ (US); Paul Pierre Bonvallet, Westfield, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/551,266

(22) Filed: Aug. 26, 2019

(65) Prior Publication Data

US 2021/0059921 A1    Mar. 4, 2021

(51) Int. Cl.
*A61K 8/73* (2006.01)
*A61Q 19/10* (2006.01)

(52) U.S. Cl.
CPC ............ *A61K 8/73* (2013.01); *A61K 2800/48* (2013.01); *A61K 2800/5922* (2013.01); *A61K 2800/596* (2013.01); *A61Q 19/10* (2013.01)

(58) Field of Classification Search
CPC ...... A61K 2800/34; A61K 8/046; A61Q 5/02; A61Q 5/12; A61Q 19/10; A61Q 19/005
See application file for complete search history.

(56) References Cited

U.S. PATENT DOCUMENTS

| | | | | |
|---|---|---|---|---|
| 5,977,037 A * | 11/1999 | Giret | ........................ | A61Q 5/02 510/122 |
| 6,627,586 B1 * | 9/2003 | Brooks | ................... | A61K 8/345 510/130 |
| 2009/0325837 A1 | 12/2009 | Mundschau et al. | | |
| 2010/0226948 A1 | 9/2010 | Jitpraphai et al. | | |
| 2010/0256033 A1 * | 10/2010 | Menard | ................ | A61K 8/0208 510/146 |
| 2014/0186284 A1 * | 7/2014 | Sha | ...................... | A61K 8/8176 424/70.13 |
| 2014/0349902 A1 | 11/2014 | Allef et al. | | |
| 2015/0157548 A1 | 6/2015 | De Feij et al. | | |
| 2017/0000710 A1 * | 1/2017 | Klug | ...................... | A61Q 5/006 |
| 2018/0116937 A1 * | 5/2018 | Park | ...................... | A61K 8/466 |

FOREIGN PATENT DOCUMENTS

| | | | |
|---|---|---|---|
| JP | 2001247449 | 9/2001 | |
| JP | 2011503007 | 1/2011 | |
| JP | 2013163659 A | 8/2013 | |
| JP | 2015098449 | 5/2015 | |
| JP | 2016199475 | 12/2016 | |
| JP | 2016540008 | 12/2016 | |
| WO | WO-2015006300 A1 * | 1/2015 | ............. A61Q 19/10 |
| WO | 2018058208 A1 | 4/2018 | |

OTHER PUBLICATIONS

Schwartz (Dermatitis from cutting oils), Division of Industrial Hygiene, National Institute of Health (Year: 1941).*
Johnson et al. "The use of fatty acid derivatives in cosmetics and toiletries", Journal of the American chemistry Society vol. 55438-433, Apr. 1978.*
PCT Notification of Transmittal of the International Search Report and the Written Opinion of the International Searching Authority, or the Declaration issued to PCT/US2020/047633 dated Nov. 24, 2020.
Mintel, "Pore Perfecting Cleansing Gel," XP055749746, Record ID No. 6460289, www.gnpd.com.

\* cited by examiner

*Primary Examiner* — Isis A Ghali
(74) *Attorney, Agent, or Firm* — McNees Wallace & Nurick LLC

(57) ABSTRACT

An inventive cleansing composition includes at least one polysaccharide derivative selected from holosides and a non-sulfated glycosaminoglycan, the at least one polysaccharide derivative, and a blend of two or more surfactants, the blend of two or more surfactants, selected from anionic surfactants, amphoteric/zwitterionic surfactants, non-ionic surfactants. The cosmetic composition may be a single phase, water-based composition, and is free or essentially free of silicones.

20 Claims, No Drawings

FATTY-OIL-FREE, LOW-FRICTION CLEANSER WITH HIGH-FOAMING PROPERTIES

FIELD OF THE INVENTION

The invention relates to a rinsible, silicone-free foaming skin cleanser that is gentle and provides a consumer-perceivable aesthetic of high glide (i.e., easy spread, low-friction) application, the cleanser being suitable for use in cleansing sensitive skin, particularly skin affected by injury, burn or medical treatment, and also suitable for make-up removal for the skin, the eyes, the scalp and/or the hair, and for treating and/or disinfecting skin and/or scalp.

BACKGROUND OF THE INVENTION

Cleansing of keratinous tissue, such as skin/scalp and hair can be achieved using a variety of products, including foaming water-based cleansers. Such products are currently available commercially as liquids, gels, creams and bars. In various forms, such products may include any one or more of silicone and non-silicone oil/fatty compounds, including silicone oils such as dimethicone, and oils and emollients including fatty acid salts, and a wide variety of surfactants. Advantages of these compositions are their cleansing ability, and the consumer-perceivable aesthetics of high-foam and creaminess. Some disadvantages of foaming cleansers include stickiness and a less than fresh feel due to residual oil after use, excessive slipperiness after rinsing caused by cationic polymer components creating the perception of poor cleansing, and tightness and dryness due to excess detergency. Some foaming cleansers are particularly formulated for gentleness to avoid at least the drying and tightness and exclude oils to avoid greasiness. But both normal-type and gentle-type foaming cleansers that lack oils also have the undesirable property of creating drag on the skin, which result in tugging and rubbing during use, causing discomfort and irritation.

Current options for cleansers include some that provide the aesthetic of relatively easy glide-on application and use but can leave behind an unpleasant and greasy skin feel, and those that leave a fresher feel but provide a sticky or tense aesthetic on application requiring pulling and tugging on skin. Thus, there remains need for rinsible cleansing products for keratinous tissues that have the desirable aesthetic properties of foaming and fresh feel after cleansing and deliver gentleness to the skin that includes the perceivable property of easy glide application without tugging and pulling and resultant irritation.

The cleansing composition according to the instant disclosure provides a low-friction, high glide gentle foaming cleanser that is free of silicones to provide good spreadability, pleasant foaming and glide aesthetic properties during cleansing, and upon rinsing, leaves a fresh and hydrated skin feel.

BRIEF SUMMARY OF THE INVENTION

The summary is provided to introduce a selection of concepts in a simplified form that are further described below in the detailed description of the invention. This summary is not intended to identify key features of the claimed subject matter, nor is it intended to be used as an aid in determining the scope of the claimed subject matter.

In accordance with various embodiments, provided is a cleansing composition for gentle cleansing of skin, particularly sensitive skin, that avoids tugging and pulling of tissue by providing a gliding, low-friction application and gentle foaming cleansing.

In the various embodiments, the cleansing composition includes:

i. at least one polysaccharide derivative selected from holosides and a non-sulfated glycosaminoglycan, the at least one polysaccharide derivative present in the cleansing composition in an amount from about 0.04% to about 2%, by weight, based on the weight of the cleansing composition; and ii. a blend of two or more surfactants, the blend of two or more surfactants present in the cleansing composition in an amount from about 4% to about 25%, by weight, based on the weight of the cleansing composition.

In accordance with the various embodiments, the cleansing composition is a single phase, water-based composition, that is free or essentially free of silicones. In some particular embodiments, the cleansing composition is devoid of silicones, such as, silicone polymers, for example selected from dimethicone and other silicone oils, and silicon elastomers.

In some embodiments, the cleansing composition is free or essentially free of any one or more of sulfates, oil/fatty compounds, and alcohols. In some particular embodiments, the cleansing composition is devoid of any one or more of sulfates, oil/fatty compounds, and alcohols.

In some embodiments, the at least one polysaccharide derivative comprising a holoside is selected from, for example, hydroxyethylcelluose, ethylcellulose, hydroxypropyl cellulose, hydroxypropyl methyl cellulose, sodium carboxymethyl cellulose, and carrageenan. In some particular embodiments, the at least one polysaccharide derivative comprising a holoside comprises at least one of hydroxyethylcelluose and hydroxypropylmethylcellulose.

In some particular embodiments, the at least one polysaccharide derivative comprising a non-sulfated glycosaminoglycan comprises at least sodium hyaluronate.

In some embodiments, the at least one polysaccharide derivative is present in the cleansing composition in an amount from about 0.1% to about 1%, by weight, based on the weight of the cleansing composition.

In some embodiments, the cleansing composition includes only one polysaccharide derivative that is one of a holoside and a non-sulfated glycosaminoglycan.

In some embodiments, the cleansing composition includes more than one polysaccharide derivative that is one of a holoside and a non-sulfated glycosaminoglycan, wherein each of the more than one polysaccharide derivative is present in the cleansing composition in an amount from about 0.04% to about 2%, by weight, based on the weight of the cleansing composition, and wherein the total amount of polysaccharide derivative in composition is present in an amount from about 0.1% to about 5%, by weight, based on the weight of the cleansing composition.

In some particular embodiments, each polysaccharide derivative is present in the cleansing composition in an amount from about 0.4% to about 0.5%.

In accordance with the various embodiments, the cleansing composition comprises a blend of surfactants. In accordance with the various embodiments, the cleansing composition comprises a blend of surfactants that comprises two or more surfactants selected from anionic, sulfate-free surfactants, amphoteric/zwitterionic surfactants, non-ionic surfactants, and combinations thereof. In some embodiments, the blend of two or more surfactants comprises surfactants that are selected from only one of anionic, sulfate-free surfactants, amphoteric/zwitterionic surfactants, non-ionic surfactants. In some embodiments, the blend of two or more surfactants comprises surfactants that are selected from at least two of anionic, sulfate-free surfactants, amphoteric/zwitterionic surfactants, non-ionic surfactants. In some embodiments, the blend of surfactants comprises only two surfactants. In some embodiments, the blend of surfactants comprises three or more surfactants.

In some embodiments, anionic sulfate-free surfactants may be selected from, for example, alkyl sulfonates, alkyl sulfosuccinates, alkyl ether sulfosuccinates, alkyl sulfoacetates, alkyl sulfosuccinamates, alkyl ether carboxylates, alkyl succinates, fatty acyl taurates, fatty acyl isethionates, fatty acyl sarcosinates, fatty acyl glutamates, fatty acyl glycinates, and alkyl phosphates.

In some embodiments, amphoteric/zwitterionic surfactants may be selected from, for example, amphocarboxylates, alkyl betaines, amidoalkyl betaines, amphophosphates, phosphobetaines, pyrophosphobetaines, carboxyalkyl polyamines, and amidoalkyl sultaines.

In some embodiments, non-ionic surfactants may be selected from, for example, alkyl polyglucosides having alkyl groups with carbon chain length from C10 to C16.

In some particular embodiments, the blend of surfactants comprises two or more surfactants that are sulfate-free.

In some particular embodiments, the blend of surfactants comprises at least one or a combination of sodium lauroyl methyl isethionate and sodium cocoamphoacetate.

In some embodiments, the blend of surfactants is present in the cleansing composition in an amount from about 6% to about 12%, by weight, based on the weight of the cleansing composition.

In accordance with the various embodiments, each one of the surfactants in the blend of surfactants is present in the cleansing composition in an amount from about 2% to about 12%, by weight, based on the weight of the cleansing composition.

In some particular embodiments, each one of the blend of surfactants is present in the cleansing composition in an amount from about 3% to about 4%. And in some embodiments, the total amount of surfactant present in the cleansing composition is in an amount from about 6% to about 8%, by weight, based on the weight of the cleansing composition.

In some embodiments, the cleansing composition includes one or more thickeners for a water-based system, selected from, for example, acrylates/beheneth-25 methacrylate copolymer, acrylates copolymer, acrylates/C10-30 alkyl acrylate crosspolymer, sodium acrylates copolymer (and) caprylic/capric triglyceride, carbomer, xanthan gum, hydroxypropyl guar, ceratonia siliqua (carob) gum, ammonium polyacryloyldimethyl taurate, ammonium acryloyldimethyltaurate/steareth-25 methacrylate crosspolymer, polyacrylate crosspolymer-6 and combinations thereof.

In some particular embodiments, the one or more thickeners, when present, comprises one or a combination of acrylates/beheneth-25 methacrylate copolymer, and acrylates copolymer.

In accordance with those embodiments that include one or more thickeners, each thickener is present in the cleansing composition in an amount from about 0.01% to about 5%, by weight, based on the weight of the cleansing composition. In some particular embodiments, each of the one or more thickeners is present in the cleansing composition in an amount from about 0.25% to about 0.75%. And in some embodiments, the total amount of thickener present in the cleansing composition in an amount from about 0.02% to about 10%, by weight, based on the weight of the cleansing composition. In some particular embodiments, the total amount of thickener is present in the cleansing composition in an amount from about 0.45% to about 1.25%%, by weight, based on the weight of the cleansing composition.

In some embodiments, the cleansing composition includes one or more hydrating agents/humectants, comprising, for example, one or more polyols. In some particular embodiments, the one or more hydrating agents/humectants, when present, comprises glycerin.

In accordance with those embodiments that include one or more hydrating agents/humectants, each hydrating agent/humectant is present in the cleansing composition in an amount from about 0.1% to about 15%, by weight, based on the weight of the cleansing composition. In some particular embodiments, each of the hydrating agents/humectants is present in the cleansing composition in an amount from about 2% to about 5%. And in some embodiments, the total amount of hydrating agent/humectant present in the cleansing composition is in an amount from about 3% to about 4%, by weight, based on the weight of the cleansing composition.

In accordance with the various embodiments, water is present in the cleansing composition in an amount from about 50% to about 95%, by weight, based on the weight of the cleansing composition. In some embodiments, water is present in the cleansing composition in an amount from at least about 75% by weight, based on the weight of the cleansing composition.

In some embodiments, the cleansing composition includes:
i. at least one polysaccharide derivative selected from holosides and a non-sulfated glycosaminoglycan, the holoside selected from hydroxyethylcelluose, ethylcellulose, hydroxypropyl cellulose, hydroxypropyl methyl cellulose, sodium carboxymethyl cellulose, and carrageenan, and the non-sulfated glycosaminoglycan comprising at least sodium hyaluronate;
ii. a blend of two or more surfactants, the blend comprising two or more surfactants selected from anionic, sulfate-free surfactants, amphoteric/zwitterionic surfactants, non-ionic surfactants, and combinations thereof.

In some particular embodiments, the cleansing composition includes:
i. at least one polysaccharide derivative selected from holosides and mucopolysaccharides, the holoside selected from hydroxyethylcelluose, ethylcellulose, hydroxypropyl cellulose, hydroxypropyl methyl cellulose, sodium carboxymethyl cellulose, and carrageenan, and the non-sulfated glycosaminoglycan comprising at least sodium hyaluronate, wherein the at least one polysaccharide derivative is present in the cleansing composition in an amount from about 0.04% to about 2%, by weight, based on the weight of the cleansing composition;
ii. a blend of two or more surfactants, the blend comprising two or more surfactants selected from anionic, sulfate-free surfactants, amphoteric/zwitterionic surfactants, non-ionic surfactants, and combinations thereof, wherein the blend of two or more surfactants is present in the cleansing composition in an amount from about 4% to about 25%, by weight, based on the weight of the cleansing composition;
iii. one or more thickeners for a water-based system;
iv. one or more humectants; and
v. water present in an amount from at least about 75% by weight, based on the weight of the cleansing composition.

In some embodiments, the cleansing composition further includes one or more additives selected from citric acid, sodium chloride; chelating agents; antimicrobial agents; neutralizing/pH-adjusting agents; vitamins; fragrances; pearlescent agents; odor absorbers; coloring materials; essential oils; fruit extracts; and combinations thereof.

In some embodiments, additives may include one or a combination of chelating agents, selected from, for example, trisodium ethylenediamine disuccinate, and triethylamine. In some embodiments, additives may include one or a combination of antimicrobial agents and their salts, selected from, for example, chlorphenesin, caprylyl glycol, phenoxyethanol, caprylhydroxamic acid, benzoic acid, salicylic acid, benzyl alcohol, phenethyl alcohol, benzalkonium chloride, 4-hydroxyacetophenone, piroctone olamine, hexyl glycerin, ethylhexylglycerin, octylglycerin, benzylglycerin, 3-heptoyl-2,2-propandiol, and 1,2-hexandiol, and pentylene glycol.

In accordance with the various embodiments, the cleansing composition demonstrates both low friction and high foam that is comparable to a silicone-containing control. More particularly, inventive composition is characterized as providing a low-frictional property exhibiting a coefficient of friction from about 0.20 up to about 0.35. In some embodiments, the coefficient of friction is demonstrated within a range of sliding speed from about 10 cm/s to about 40 cm/s using ring on plate tribology measurements with load force of 5 N. In some embodiments, the inventive composition is characterized as providing a foaming profile in a range from about at least 90 mm, or from about at least 95 mm to greater than 100 mm. In some embodiments, the foaming profile is obtained with a composition at a 10× dilution after 15 seconds of agitation at a speed of about 8000 rpm.

Other features and advantages of the present invention will be apparent from the following more detailed description, by way of example, the principles of the invention.

This disclosure describes particular embodiments in accordance with the general inventive concepts and is not intended to limit the scope of the invention in any way. Indeed, the invention as described in the specification is broader than and unlimited by the particular embodiments set forth herein, and the terms used herein have their full ordinary meaning.

DETAILED DESCRIPTION OF THE INVENTION

The term "at least one polysaccharide derivative" means and refers to polysaccharides that are selected from holosides and mucopolysaccharides, in particular, non-sulfated glycosaminoglycans.

The term "silicone-free" as used herein means that silicone has not been added as a component. In some embodiments, a composition is devoid of silicone. Those of skill in the art will appreciate that silicone may be present in a composition via its presence in one or more of the formulation components; thus, in some embodiments a composition may be "essentially silicone-free" wherein silicone is present at a concentration that does not exceed 5% by weight, and in some instances is present not more than 3% by weight, and in some instances is present not more than 1% by weight, based on the weight of the cleansing composition. In some particular embodiments "silicone-free" means that the cleansing composition is free, essentially free or devoid specifically of silicones, such as silicone polymers, for example selected from dimethicone and other silicone oils, and silicon elastomers.

The term "sulfate-free" as used herein means that sulfate has not been added as a component. In some embodiments, a composition is devoid of sulfate. Those of skill in the art will appreciate that sulfate may be present in a composition via its presence in one or more of the formulation components; thus, in some embodiments a composition may be "essentially sulfate-free" wherein sulfate is present at a concentration that does not exceed 5% by weight, and in some instances is present not more than 3% by weight, and in some instances is present not more than 1% by weight, based on the weight of the cleansing composition. In some particular embodiments "sulfate-free" means that the polysaccharide derivative and surfactant components thereof do not include sulfate.

The term "oil-free" as used herein means that oil has not been added as a component. In some embodiments, a composition is devoid of oil. Those of skill in the art will appreciate that oil may be present in a composition via its presence in one or more of the formulation components; thus, in some embodiments a composition may be "essentially oil-free" wherein oil is present at a concentration that does not exceed 5% by weight, and in some instances is present not more than 3% by weight, and in some instances is present not more than 1% by weight, based on the weight of the cleansing composition.

The term "alcohol-free" as used herein means that alcohol has not been added as a component. In some embodiments, a composition is devoid of alcohol. Those of skill in the art will appreciate that alcohol may be present in a composition via its presence in one or more of the formulation components; thus, in some embodiments a composition may be "essentially alcohol -free" wherein alcohol is present at a concentration that does not exceed 5% by weight, and in some instances is present not more than 3% by weight, and in some instances is present not more than 1% by weight, based on the weight of the cleansing composition. In some particular embodiments "alcohol-free" means that the cleansing composition is free, essentially free or devoid specifically of alcohols comprising one or more of ethanol and isopropyl alcohol.

"Keratinous substrate" and "keratinous tissue" each includes but is not limited to skin, scalp, hair, and nails.

In some embodiments, cleansers are used on one or more of the parts of or the entire body, the face, the hair and/or scalp, and discrete body parts. Cleansers may be used on "normal" (i.e., not dry, oily, sensitive or inured skin) or on skin that is other than normal, and for example, may be sensitive due to injury, allergy, dermatitis, chemical and contact sensitivities, burns, and post medical treatment. Particularly for sensitive tissues, it is desirable to provide rinsible cleansing products that have desirable consumer-perceivable aesthetic properties that include foaming, easy glide application, minimal tugging and pulling during cleansing, and fresh feel after cleansing, without tightness and drying.

The cleansing composition according to the instant disclosure provides a low-friction, high glide gentle foaming cleanser that is free of silicones to provide good spreadability, pleasant foaming and glide aesthetic properties during cleansing, and upon rinsing, leaves a fresh and hydrated skin feel. This composition advantageously delivers a blend of components that are gentle to the skin, with pleasing foam and unexpectedly high glide that is in some embodiments seen in silicone oil-based formulations. Moreover, the cleansing composition provides significantly enhanced glide as compared with commercially available gentle cleansing formulations.

In accordance with the various embodiments, the cosmetic composition is a single phase, water-based composition, that is free or essentially free of silicones. In some particular embodiments, the composition is devoid of silicones, such as, silicone polymers, for example selected from dimethicone and other silicone oils, and silicon elastomers.

In some embodiments, the cleansing composition is free or essentially free of any one or more of sulfates, oils/oil/fatty compounds, and alcohols. In some particular embodiments, the composition is devoid of any one or more of sulfates, oil/fatty compounds, and alcohols.

In various embodiments, the cleansing composition includes at least one polysaccharide derivative selected from holosides and a non-sulfated glycosaminoglycan, the at least one polysaccharide derivative present in the cleansing composition in an amount from about 0.04% to about 2%, by weight, based on the weight of the cleansing composition; and a blend of two or more surfactants, the blend of two or more surfactants present in the cleansing composition in an amount from about 4% to about 25%, by weight, based on the weight of the cleansing composition.

In some embodiments, the cleansing composition includes: at least one polysaccharide derivative selected from holosides and a non-sulfated glycosaminoglycan, the holoside selected from hydroxyethylcelluose, ethylcellulose, hydroxypropyl cellulose, hydroxypropyl methyl cellulose, sodium carboxymethyl cellulose, and carrageenan, and the non-sulfated glycosaminoglycan comprising at least sodium hyaluronate; and a blend of two or more surfactants, the blend comprising two or more surfactants selected from anionic, surfactants, amphoteric/zwitterionic surfactants, non-ionic surfactants, and combinations thereof.

In some embodiments, water is present in an amount from at least about 75% by weight, based on the weight of the cleansing composition.

In various embodiments, the cleansing composition may include more than one of each of the foregoing components, and may further include one or more additives including preservatives, fragrances, actives, and pH adjusters, among other cosmetically acceptable additives.

In accordance with the various embodiments, the cleansing composition demonstrates both low friction and high foam that is comparable to a silicone-containing control. More particularly, inventive composition is characterized as providing a low-frictional property exhibiting a coefficient of friction from about 0.20 up to about 0.35. In some embodiments, the coefficient of friction is demonstrated within a range of sliding speed from about 10 cm/s to about 40 cm/s using ring on plate tribology measurements with load force of 5 N.

In accordance with the various embodiments, the cleansing composition is characterized as providing a foaming profile in a range from about at least 90 mm, or from about at least 95 mm to greater than 100 mm. In some embodiments, the foaming profile is obtained with a composition at a 10× dilution after 15 seconds of agitation at a speed of about 8000 rpm.

Polysaccharide Derivative

The cleansing composition, according to the present invention, includes at least one polysaccharide derivative selected from holosides and a non-sulfated glycosaminoglycan.

As utilized herein, "holoside compound" includes holoside compounds and derivatives thereof. Suitable holoside compounds or derivatives thereof are chosen from known polysaccharides, disaccharides, or a combination thereof. Particularly suitable holoside compounds include methylcellulose, hydroxypropylmethylcellulose (HPMC), hydroxypropylcellulose (HPC) cellulose gum (CG), carrageenan, xanthan gum, and/or a combination thereof. In some embodiments, the at least one polysaccharide derivative comprising a holoside is selected from, for example, hydroxyethylcelluose, ethylcellulose, hydroxypropyl cellulose, hydroxypropyl methyl cellulose, sodium carboxymethyl cellulose, and carrageenan. In some particular embodiments, the at least one polysaccharide derivative comprising a holoside comprises at least one of hydroxyethylcelluose and hydroxypropylmethylcellulose. In some particular embodiments, the at least one polysaccharide derivative comprising a non-sulfated glycosaminoglycan comprises at least sodium hyaluronate.

Each of the at least one polysaccharide derivative selected from holosides and a non-sulfated glycosaminoglycan present in the cleansing composition according to the present invention is present in an amount of at least 0.04% by weight, or at least about 0.3% by weight, or at least about 0.4% by weight, or at least about 0.5% by weight, or at least about 0.75% by weight, or at least about 1.0% by weight, or at least about 2.0% by weight, or at least about 2.5% by weight, or from about 0.04% to about 2%, or from about 0.1% to about 5%, or from about 0.25% to 1.5%, or from about 0.1% to about 1.0%, or from about 0.4% to about 0.5%, or any suitable combination, sub-combination, range, or sub-range thereof by weight, based on the weight of the cleansing composition. One of ordinary skill in the art, however, will appreciate that other ranges are within the scope of the invention.

Thus, each of the at least one polysaccharide derivative, alone or in combination, is present in an amount by weight, based on the total weight of the cleansing composition, from about 0.04, 0.05, 0.06, 0.07, 0.08, 0.09, 0.10, 0.20, 0.30, 0.40, 0.50, 0.60, 0.70, 0.80, 0.90, 1.0, 2, 3, 4, to about 5 weight percent, including increments and ranges therein and there between.

Surfactant

In accordance with the disclosure, the cleansing composition includes one or more surfactants selected from anionic surfactants, amphoteric/zwitterionic surfactants, and non-ionic surfactants as described herein below. In accordance with the various embodiments, the cleansing composition comprises a blend of surfactants that comprises two or more surfactants selected from anionic surfactants, amphoteric/zwitterionic surfactants, non-ionic surfactants, and combinations thereof. In some embodiments, the blend of two or more surfactants comprises surfactants that are selected from only one of anionic surfactants, amphoteric/zwitterionic surfactants, non-ionic surfactants. In some embodiments, the blend of two or more surfactants comprises surfactants that are selected from at least two of anionic surfactants, amphoteric/zwitterionic surfactants, non-ionic surfactants. In some embodiments, the blend of surfactants comprises only two surfactants. In some embodiments, the blend of surfactants comprises three or more surfactants.

In some embodiments, anionic surfactants may be selected from, for example, alkyl sulfonates, alkyl sulfosuccinates, alkyl ether sulfosuccinates, alkyl sulfoacetates, alkyl sulfosuccinamates, alkyl ether carboxylates, alkyl succinates, fatty acyl taurates, fatty acyl isethionates, fatty acyl sarcosinates, fatty acyl glutamates, fatty acyl glycinates, and alkyl phosphates.

In some embodiments, amphoteric/zwitterionic surfactants may be selected from, for example, amphocarboxylates, alkyl betaines, amidoalkyl betaines, amphophosphates, phosphobetaines, pyrophosphobetaines, carboxyalkyl polyamines, and amidoalkyl sultaines.

In some embodiments, non-ionic surfactants may be selected from, for example, alkyl polyglucosides having alkyl groups with carbon chain length from C10 to C16.

In some embodiments, surfactants selected according to the disclosure are sulfate free. In some particular embodiments, the blend of surfactants comprises two or more surfactants that are sulfate-free.

In some particular embodiments, the blend of surfactants comprises at least one or a combination of sodium lauroyl methyl isethionate and sodium cocoamphoacetate.

In some embodiments, the blend of surfactants is present in the composition in an amount from about 4% to about 25%, or from about 6% to about 12%, or from about 6% to about 8% or any suitable combination, sub-combination, range, or sub-range thereof by weight, based on the weight of the cleansing composition. In accordance with the various embodiments, each one of the surfactants in the blend of surfactants is present in the composition in an amount from about 2% to about 12%, or from about 3% to about 4%, or any suitable combination, sub-combination, range, or sub-range thereof by weight, based on the weight of the cleansing composition. One of ordinary skill in the art, however, will appreciate that other ranges are within the scope of the invention.

Thus, each one of the surfactants, alone or in combination, is present in an amount by weight, based on the total weight of the cleansing composition, from about 2, 3, 4, 5, 6, 7, 8, 9, 10, 11, 12, 13, 14, 15, 16, 17, 18, 19, 20, 21, 22, 23, 24, to about 25 weight percent, including increments and ranges therein and there between.

Thickener

In accordance with the disclosure, compositions according to the disclosure can include at least one thickener.

In some embodiments, the composition includes one or more thickeners for a water-based system, selected from, for example, acrylates/beheneth-25 methacrylate copolymer, acrylates copolymer, acrylates/C10-30 alkyl acrylate crosspolymer, sodium acrylates copolymer (and) caprylic/capric triglyceride, carbomer, xanthan gum, hydroxypropyl guar, ceratonia siliqua (carob) gum, ammonium polyacryloyldimethyl taurate, ammonium acryloyldimethyltaurate/steareth-25 methacrylate crosspolymer, polyacrylate crosspolymer-6 and combinations thereof. In some embodiments the cleansing composition comprises two or more thickeners.

In some particular embodiments, the one or more thickeners, when present, comprises one or a combination of acrylates/beheneth-25 methacrylate copolymer, and acrylates copolymer.

In accordance with those embodiments that include one or more thickeners, each thickener is present in the composition in an amount from about 0.01% to about 5%, or from about 0.01% to about 3%, or from about 0.05% to about 2.5%, or from about 0.25% to about 0.75%, or any suitable combination, sub-combination, range, or sub-range thereof by weight, based on the weight of the cleansing composition. And in some embodiments, the total amount of thickener present in the composition in an amount from about 0.02% to about 10%, from about 0.01% to about 5%, or from about 1.0% to about 3%, or from about 2% to about 2.55%, or from about 0.45% to about 1.25%, or any suitable combination, sub-combination, range, or sub-range thereof by weight, based on the weight of the cleansing composition. One of ordinary skill in the art, however, will appreciate that other ranges are within the scope of the invention.

Thus, one or more thickener, when present, is present by weight, based on the total weight of the cleansing composition, from about 0.01, 0.02, 0.03, 0.04, 0.05, 0.06, 0.07, 0.08, 0.09, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5 to about 5.0 percent, including increments and ranges therein and there between.

Solvent/Water

In accordance with the various embodiments, water is present in the cleansing compositions in a range from about 40% to about 95%, or from about 50% to about 90%, or from about 55% to about 85%, or from about 60% to about 75%, or from about 65% to about 70%, or any suitable combination, sub-combination, range, or sub-range thereof by weight, based on the weight of the cleansing composition. In some embodiments, water is present in the composition in an amount from at least about 75% by weight, based on the weight of the composition. One of ordinary skill in the art, however, will appreciate that other ranges are within the scope of the invention. Thus, water is present, by weight, based on the total weight of the cleansing composition, from about 40, 45, 50, 55, 60, 65, 70, 75, 80, 85, 90 to about 95 weight percent, including increments and ranges therein and there between.

The water used may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

The pH of the cleansing composition is not limited but is generally between 2 and 12, and in some embodiments, is one of between 3 and 11, and between 5 and 9, and between 6 and 8, and in some embodiments is 7. The pH can be adjusted to the desired value by addition of a base (organic or inorganic) to the cleansing composition, for example ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid.

In some embodiments, the cleansing composition can include one or more additional solvents, for example, caprylyl glycol.

In some embodiments, the cleansing composition is free or essentially free of any and all alcohols. In some particular embodiments, the cleansing composition is free or essentially free of alcohols comprising one or more of ethanol and isopropyl alcohol.

Hydrating Agent/Humectant

In some embodiments, the composition includes one or more hydrating agents/humectants, comprising, for example, one or more polyols. In various embodiments, hydrating agents/humectants, when present may be selected from, for example, glycerin, glycerol, butylene glycol, propylene glycol, isoprene glycol, dipropylene glycol, hexylene glycol and polyethylene glycols, monoethylene glycol, diethylene glycol, triethylene glycol, diethylene glycol, hexylene glycol, glycol ethers such as monopropylene, dipropylene and tripropylene glycol alkyl(C1-C4)ethers, squalane, triacetin, sugars, such as glucose, xylitol, maltitol, sorbitol, sucrose pentaerythritol, inositol, pyrrolidone carboxylic acid, lactic acid, lithium chloride, acetamide MEA, sodium lactate, urea, dicyanamide, hyaluronic acid, aloe vera, honey, and seaweed extract.

In some embodiments, the cleansing compositions include a humectant comprising glycerin.

In accordance with the various embodiments, the amount of humectant present in the cleansing compositions can range from about 1% to about 15%, or from about 2% to about 12%, or from about 2% to about 5%, or from about 3% to about 7%, or from about 3% to about 4%, or from about 4% to about 5%, or any suitable combination, sub-combination, range, or sub-range thereof by weight, based on the weight of the cleansing composition. One of ordinary skill in the art, however, will appreciate that other ranges are within the scope of the invention.

Thus, any one of or a combination of humectant may be present, by weight, based on the total weight of the cleansing composition, is from about 1, 2, 3, 4, 5, 6, 7, 8, 9, 10, 11, 12, 13, 14, to about 15 weight percent, including increments and ranges therein and there between.

Chelating Agents

In accordance with the disclosure, in some embodiments, one or more other components comprising chelating agents can be present in the cleansing composition according to the disclosure. In some particular embodiments, chelating agents are selected from sodium phytate, ethylenediaminetetraacetic acid (EDTA), tetrasodium etidronate, tetrasodium pyrophosphate, pentasodium ethylenediamine tetramethylene phosphonate, sodium staminate and combinations of these.

In some particular embodiments, chelating agents comprise sodium phytate.

In accordance with the various embodiments, the amount of chelating agents present in the cleansing composition can be present in the cleansing composition according to the disclosure in a range from about 0.01% to about 5% by weight, or from about 0.05% to about 2% by weight, or from about 0.10% to about 1%, or from about 0.15% to about 0.5%, and from about 0.15% to about 0.2%, or any suitable combination, sub-combination, range, or sub-range thereof by weight, based on the weight of the cleansing composition.

Thus, one or a combination of chelating agents may be present, by weight, based on the total weight, each one or the combination present from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2.0, 3.0, 4.0 up to about 5.0 weight percent, including increments and ranges therein and there between.

Optional Additives

The cleansing compositions can also comprise one or more additives selected from citric acid, sodium chloride; chelating agents; antimicrobial agents; neutralizing/pH-adjusting agents; vitamins; fragrances; pearlescent agents; odor absorbers; coloring materials; essential oils; fruit extracts; and combinations thereof.

In some embodiments, additives may include one or a combination of chelating agents, selected from, for example, trisodium ethylenediamine disuccinate, and triethylamine.

In some embodiments, additives may include one or a combination of antimicrobial agents and their salts, selected from, for example, chlorphenesin, caprylyl glycol, phenoxyethanol, caprylhydroxamic acid, benzoic acid, salicylic acid, benzyl alcohol, phenethyl alcohol, benzalkonium chloride, 4-hydroxyacetophenone, piroctone olamine, hexyl glycerin, ethylhexylglycerin, octylglycerin, benzylglycerin, 3-heptoyl-2,2-propandiol, and 1,2-hexandiol, and pentylene glycol.

In accordance with the various embodiments, the amount of one or more actives and additives, alone or in combination, present in the cleansing composition can be present in the cleansing composition according to the disclosure in a range from about 0.001% to about 20%, by weight, or from about 0.005% to about 0.01%, or from about 0.01% to about 0.1%, or from about 0.15% to about 5%, or from about 0.40% to about 4%, or from about 0.5% to about 2.5% by weight, or from about 1% to about 2%, or any suitable combination, sub-combination, range, or sub-range thereof by weight, based on the total weight of the cleansing composition.

Thus, any one or a combination of actives and additives may be present, by weight, based on the total weight of the cleansing composition, each one or the combination present from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

EXAMPLES

Example 1

Raw Materials

TABLE 1

| Raw Materials INCI (or Commercial Name) |
| --- |
| PEG-12 Dimethicone (water soluble silicone) as comparative reference |
| Sodium Hyaluronate |
| Hydroxyethylcelluose |
| Hydroxypropylmethyl cellulose |
| CeraVe Hydrating Cleanser (TM) |
| Cetaphil Gentle Cleanser (TM) |
| Philosophy Purity Made Simple (TM) |
| Prescribed Solutions Post-Procedure Cleanser (TM) |

Example 2

Inventive Compositions

Various representative embodiments of the inventive compositions are exemplified herein in Table 2. In the exemplified embodiments, the cleansing composition is a single-phase cleanser in a water-based solvent that is free of silicone.

TABLE 2

| INCI (US/UE) | COMPARATIVE CONTROL (WITH SILICONE) | INVENTIVE 1 | INVENTIVE 2 | INVENTIVE 3 |
|---|---|---|---|---|
| Inventive Compositions | | | | |
| PEG-12 DIMETHICONE | 1.50 | | | |
| ADDITIVES (ONE OR MORE OF) TRISODIUM ETHYLENEDIAMINE DISUCCINATE; CITRIC ACID; SODIUM HYDROXIDE; SODIUM BENZOATE; SODIUM CHLORIDE | 1.14 | 2.04 | 2.04 | 2.04 |
| SODIUM LAUROYL METHYL ISETHIONATE | 3.35 | 3.35 | 3.35 | 3.35 |
| ANTIMICROBIAL SYSTEM | 1.10 | 1.10 | 1.10 | 1.10 |
| GLYCERIN | 4.00 | 4.00 | 4.00 | 4.00 |
| SODIUM COCOAMPHOACETATE | 3.04 | 3.04 | 3.04 | 3.04 |
| WATER/AQUA | QS | QS | QS | QS |
| ACRYLATES/BEHENETH-25 METHACRYLATE COPOLYMER | 1.80 | | | |
| SODIUM HYALURONATE | | | | 0.10 |
| ACRYLATES COPOLYMER | | 2.70 | 2.40 | 2.70 |
| HYDROXYETHYLCELLULOSE | | 0.50 | | |
| HYDROXYPROPYL METHYLCELLULOSE | | | 0.478 | |
| Coefficient of Friction* | 0.2-0.26 | 0.3-0.35 | 0.22-0.25 | 0.22-0.23 |
| Foam Height (mm) | 100.8 | 95.4 | 100.2 | 97.7 |

Referring to Table 2, Inventive Compositions 1, 2 and 3 share the same base that includes the exemplified surfactant blend, with water based polymeric thickeners, polyol humectant, a blend of antimicrobials, chelating and conditioning agents, in water, and wherein the polysaccharide derivative is varied.

Generally, in some representative embodiments, inventive compositions are prepared by steps that include dispersing the polysaccharide in water. Thereafter, additives, including, for example, preservatives, and other solvents are mixed in until dissolved. Thereafter, thickening polymer(s) are added and ad mixed until well-dispersed. The pH is adjusted to neutralize the polymer (if necessary). Thereafter, surfactant(s) are added, and the batch stirred until uniform.

Example 3

Comparative Compositions

Exemplary embodiments of inventive compositions in the form of cleansing and makeup removing compositions (not imbued in a substrate) according to the disclosure are provided in Table 3.

TABLE 3

| COMPARATIVE COMPOSITION | COMMERCIAL NAME | INGREDIENTS |
|---|---|---|
| Comparative Compositions | | |
| COMPARATIVE 1 | CeraVe Hydrating Cleanser (TM) | Water (Purified), Glycerin, Behentrimonium Methylsulfate/Cetearyl Alcohol, Ceramide 3, Ceramide 6 11, Ceramide 1, Hyaluronic Acid, Cholesterol, Polyoxyl 40 Stearate, Glyceryl Monostearate, Stearyl Alcohol, Polysorbate 20, Potassium Phosphate, Dipotassium Phosphate, Sodium Lauroyl Lactylate, Cetearyl Alcohol, Disodium EDTA, Phytosphingosine, Methylparaben, Propylparaben, Carbomer, Xanthan Gum |
| COMPARATIVE 2 | Cetaphil Gentle Cleanser (TM) | Water, Cetyl Alcohol, Propylene Glycol, Sodium Lauryl Sulfate, Stearyl Alcohol, Methylparaben, Propylparaben, Butylparaben |
| COMPARATIVE 3 | Philosophy Purity Made Simple (TM) | Water, Sodium Lauroamphoacetate, Sodium Trideceth Sulfate, *Limnanthes Alba* (Meadowfoam) Seed Oil, Coco-Glucoside, Coconut Alcohol, Peg-120 Methyl Glucose Dioleate, Glycerin, Carbomer, Isopropyl |

TABLE 3-continued

Comparative Compositions

| COMPARATIVE COMPOSITION | COMMERCIAL NAME | INGREDIENTS |
|---|---|---|
| COMPARATIVE 4 | Prescribed Solutions Post-Procedure Cleanser (TM) | Alcohol, Polysorbate 20, Citric Acid, Imidazolidinyl Urea, Methylparaben, *Aniba Rosaeodora* (Rosewood) Wood Oil, Propylparaben, Triethanolamine, *Amyris Balsamifera* Bark Oil, *Bulnesia Sarmientoi* Wood Oil, *Cymbopogon Martini* Oil, *Pelargonium Graveolens* Flower Oil, *Rosa Centifolia* Flower Oil, *Santalum Album* (Sandalwood) Oil, *Daucus Carota* Sativa (Carrot) Seed Oil, *Mimosa Tenuiflora* Bark Extract, *Ormenis Multicaulis* Oil, *Piper Nigrum* (Pepper) Fruit Oil, *Salvia Sclarea* (Clary) Oil, Fd&C Yellow No. 5 (Ci 19140). Water (Aqua), Sodium Lauryl Glucose Carboxylate, Lauryl Glucoside, Cocamidopropyl Betaine, Propylene Glycol, Coco-Glucoside, Glyceryl Oleate, 1,2-Hexanediol, Caprylyl Glycol, PEG-150 Distearate, Panthenol, Potassium Sorbate, Dimethicone, Polyquaternium-10, Disodium EDTA |

Referring to Table 2, comparative composition 1 is a commercially available competitive product sold under the brand CERAVE HYDRATING CLEANSER™; comparative composition 2 is a commercially available competitive product sold under the brand CETAPHIL GENTLE CLEANSER™, comparative composition 3 is a commercially available competitive product sold under the brand PHILOSOPHY PURITY MADE SIMPLE™, and comparative composition 4 is a commercially available competitive product sold under the brand PRESCRIBED SOLUTIONS POST-PROCEDURE CLEANSER™.

Example 4

Tribology and Foaming Properties of Inventive and Comparative Compositions

Studies were conducted with each of the exemplified inventive and comparative compositions, and raw materials dispersed in water, as referenced in the tables below, to evaluate their tribology and foaming properties. The results are shown in Tables 4-6. As referenced herein, HEC is Hydroxyethylcelluose, HPMC is Hydroxypropylmethylcellulose, and HLA is Hyaluronic acid.

Amounts of indicated ingredients represent percent of ingredient, by weight, based on the total weight of the cleansing composition or dispersion.

Tribology measurements were made on neat cleanser (inventive and comparative, each in liquid phase without dilution), and RM dispersions, with a range of sliding speed from about 10 cm/s to about 40 cm/s using ring on plate tribology measurements with load force of about 5 N.

Foaming was determined using a Kruss Dynamic Foam Analyzer with a sample size of 50 ml. Cleanser was diluted 10×, then was agitated at high speed for about 15 seconds before stopping; foam height was measured 5 seconds later. More particularly, a foaming profile for a tested cleansing composition is determined as a measure of foam height produced with about 50 ml of the cleansing composition in a 10× dilution with water, wherein the diluted cleansing composition is agitated at high speed (8000 rpm) for about 15 seconds before stopping, and about 5 seconds after agitation is stopped, foam height is measured from the meniscus of the diluted cleansing composition, for example using a Kruss Dynamic Foam Analyzer.

TABLE 4

Tribology and foaming data for inventive compositions.

| | PEG-12 Dimethicone | HEC | HPMC | HLA | Coefficient of Friction* | Foam Height (mm) |
|---|---|---|---|---|---|---|
| COMPARATIVE CONTROL | 1.5 | 0 | 0 | 0 | 0.2-0.26 | 100.8 |
| INV 1 | 0 | 0.5 | 0 | 0 | 0.3-0.35 | 95.4 |
| INV 2 | 0 | 0 | 0.5 | 0 | 0.22-0.25 | 100.2 |
| INV 3 | 0 | 0 | 0 | 0.1 | 0.22-0.23 | 97.7 |

Referring to Table 4, inventive compositions demonstrated both low friction and high foam comparable to the silicone containing comparative control. More particularly, inventive compositions are characterized as providing a low-frictional property exhibiting a coefficient of friction from about 0.20 up to about 0.35 within a range of sliding speed from about 10 cm/s to about 40 cm/s using ring on plate tribology measurements with load force of 5 N. And inventive compositions are characterized as providing a foaming profile of at least 95 mm at a 10× dilution after 15 seconds of agitation at a speed of about 8000 rpm.

Referring to the tables, results obtained with inventive compositions (Table 4) and comparatives and raw materials (Tables 5 and 6), show that the coefficient of friction during rubbing seen in the inventive compositions is essentially the same as that of a water-soluble silicone (COMPARATIVE CONTROL), each of which is appreciably lower than the coefficient of friction for water alone. When compared to comparative formulations, the inventive compositions demonstrate a coefficient of friction during rubbing that is the same or significantly better, and uniformly demonstrate significantly better foam than any of the comparative formulations.

TABLE 5

Tribology and foaming data for comparative compositions.

| | Coefficient of Friction* | Foam Height (mm) |
|---|---|---|
| COMPARATIVE 1 | 0.24-0.25 | 41.1 |
| COMPARATIVE 2 | 0.26-0.59 | 36.6 |
| COMPARATIVE 3 | 0.26-0.31 | 48.7 |
| COMPARATIVE 4 | 0.42-0.48 | 62.2 |

Referring to Table 4, comparative composition 1, CERAVE HYDRATING CLEANSER™, contains a cationic surfactant, Behentrimonium Methylsulfate/Cetearyl Alcohol, known to impart a conditioning and slippery feel to products. This slip is likely the primary contributor to lower friction observed in the data; comparative composition 2, CETAPHIL GENTLE CLEANSER™, contains what are deemed to be gentle cleansing components but which has significant friction based on tribology results; comparative composition 3, PHILOSOPHY PURITY MADE SIMPLE™, contains several oils known to provide slip and glide; comparative composition 4, PRESCRIBED SOLUTIONS POST-PROCEDURE CLEANSER™, contains silicone to provide slip and glide, and a cationic polymer, Dimethicone, Polyquaternium-10, which may lower friction slightly in addition to the silicone.

TABLE 6

Tribology and foaming data for raw materials dispersed in water.

| RM- water dispersion composition | PEG-12 Dimethicone | HEC | HPMC | HLA | Water | Coefficient of Friction* | Foam Height (mm) |
|---|---|---|---|---|---|---|---|
| A | 2 | 0 | 0 | 0 | QS | 0.21-0.26 | N/A |
| B | 0 | 0 | 0 | 0.35 | QS | 0.23-0.29 | N/A |
| C | 0 | 1 | 0 | 0 | QS | 0.20-0.29 | N/A |
| D | 0 | 0 | 1 | 0 | QS | 0.22-0.26 | N/A |
| E | 0 | 0.2 | 0 | 0 | QS | 0.2-0.37 | N/A |
| F | 0 | 0 | 0.2 | 0 | QS | 0.25-0.39 | N/A |
| G | 0.2 | 0 | 0 | 0 | QS | 0.16-0.18 | N/A |
| H | 0 | 0 | 0 | 0.04 | QS | 0.18-0.23 | N/A |
| I | 0 | 0.04 | 0 | 0 | QS | 0.21-0.34 | N/A |
| J | 0 | 0 | 0.04 | 0 | QS | 0.21-0.35 | N/A |
| K | 0.04 | 0 | 0 | 0 | QS | 0.3-0.34 | N/A |
| Control (Water only) | 0 | 0 | 0 | 0 | QS | 0.32-0.65 | N/A | article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"One or more," as used herein, means at least one, and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All materials and methods described herein that embody the present invention can, in alternate embodiments, be more specifically defined by any of the transitional terms "comprising," "consisting essentially of," and "consisting of."

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material The articles "a" and "an," as used herein, mean one or more when applied to any feature in embodiments of the present invention described in the specification and claims. The use of "a" and "an" does not limit the meaning to a single feature unless such a limit is specifically stated. The comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

While the invention has been described with reference to a preferred embodiment, it will be understood by those skilled in the art that various changes may be made, and equivalents may be substituted for elements thereof without departing from the scope of the invention. In addition, many modifications may be made to adapt a particular situation or material to the teachings of the invention without departing from the essential scope thereof. Therefore, it is intended that the invention is not limited to the particular embodiment disclosed as the best mode contemplated for carrying out this invention, but that the invention will include all embodiments falling within the scope of the appended claims.

What we claim:

1. A cleansing composition, comprising:
   i. at least one polysaccharide derivative selected from the group consisting of holosides, non-sulfated glycosaminoglycans, and combinations thereof, the at least one polysaccharide derivative present in the cleansing composition in an amount from about 0.04% to about 2%, by weight, based on the weight of the cleansing composition;
   ii. a blend of two or more surfactants consisting essentially of two or more anionic surfactants, two or more amphoteric surfactants, or at least one anionic surfactant and at least one amphoteric surfactant, the blend of two or more surfactants being present in the cleansing composition in an amount from about 4% to about 12%, by weight, based on the weight of the cleansing composition, and
   iii at least one humectant present in the cleansing composition in an amount from 1% to 15%, by weight, based on the weight of the cleansing composition, wherein the cleansing composition is free of fatty oil compounds, the cleansing composition is free of fatty acid salts, and the cleansing composition has a low-frictional property exhibiting a coefficient of friction from about 0.20 up to about 0.35.

2. The cleansing composition in accordance with claim 1, wherein the cleansing composition is a single phase, water-based composition, that is free or essentially free of silicones, free of cationic polymers comprising Polyquaternium-10, and free of cocamidopropyl betaine.

3. The cleansing composition in accordance with claim 1, wherein the at least one polysaccharide derivative comprises a holoside selected from the group consisting of hydroxyethylcelluose, ethylcellulose, hydroxypropyl cellulose, hydroxypropyl methyl cellulose, sodium carboxymethyl cellulose, carrageenan, and combinations thereof.

4. The cleansing composition in accordance with claim 1, wherein the at least one polysaccharide derivative comprises a holoside that comprises hydroxyethylcelluose, hydroxypropylmethylcellulose or a combination thereof.

5. The cleansing composition in accordance with claim 1, wherein the at least one polysaccharide derivative comprises a non-sulfated glycosaminoglycan that comprises at least sodium hyaluronate.

6. The cleansing composition in accordance with claim 1, wherein at least one polysaccharide derivative is present in the cleansing composition in an amount from about 0.1% to about 1%, by weight, based on the weight of the cleansing composition.

7. The cleansing composition in accordance with claim 1, wherein the cleansing composition includes only one polysaccharide derivative that is one of a holoside or a non-sulfated glycosaminoglycan.

8. The cleansing composition in accordance with claim 1, wherein the cleansing composition includes more than one polysaccharide derivative that is one of a holoside or a non-sulfated glycosaminoglycan, wherein each of the more than one polysaccharide derivative is present in the cleansing composition in an amount from about 0.04% to about 2%, by weight, based on the weight of the cleansing composition, and wherein the total amount of polysaccharide derivative in the composition is present in an amount from about 0.1% to about 5%, by weight, based on the weight of the cleansing composition.

9. The cleansing composition in accordance with claim 1, wherein each of the at least one polysaccharide derivative is present in the cleansing composition in an amount from about 0.4% to about 0.5%.

10. The cleansing composition in accordance with claim 1, wherein the blend of surfactants consists essentially of at least one anionic surfactant and at least one amphoteric surfactant, and, wherein the at least one anionic surfactant is selected from the group consisting of alkyl sulfonates, alkyl sulfosuccinates, alkyl ether sulfosuccinates, alkyl sulfoacetates, alkyl sulfosuccinamates, alkyl ether carboxylates, alkyl succinates, fatty acyl taurates, fatty acyl isethionates, fatty acyl sarcosinates, fatty acyl glutamates, fatty acyl glycinates, alkyl phosphates, and combinations thereof, and, wherein the at least one amphoteric surfactant is selected from the group consisting of amphocarboxylates, alkyl betaines, amidoalkyl betaines, amphophosphates, phosphobetaines, pyrophosphobetaines, carboxyalkyl polyamines, amidoalkyl sultaines, and combinations thereof.

11. The cleansing composition in accordance with claim 1, wherein each one of the blend of surfactants is present in the cleansing composition in an amount from about 3% to about 4%, and wherein the total amount of surfactant present in the cleansing composition is in an amount from about 6% to about 8%, by weight, based on the weight of the cleansing composition.

12. The cleansing composition in accordance with claim 1, wherein the cleansing composition incudes one or more thickeners for a water-based system, selected from the group consisting of acrylates/beheneth-25 methacrylate copolymer, acrylates copolymer, acrylates/C10-30 alkyl acrylate crosspolymer, sodium acrylates copolymer (and) caprylic/capric triglyceride, carbomer, xanthan gum, hydroxypropyl guar, ceratonia siliqua (carob) gum, ammonium polyacryloyldimethyl taurate, ammonium acryloyldimethyltaurate/steareth-25 methacrylate crosspolymer, polyacrylate crosspolymer-6, and combinations thereof.

13. The cleansing composition in accordance with claim 12, wherein each of the one or more thickeners is present in the cleansing composition in an amount from about 0.25% to about 0.75%, and wherein the total amount of thickener is present in the cleansing composition in an amount from about 0.45% to about 1.25%, all percentages by weight, based on the weight of the cleansing composition.

14. The cleansing composition according to claim 1, wherein the coefficient of friction is demonstrated within a range of sliding speed from about 10 cm/s to about 40 cm/s using ring on plate tribology measurements with load force of 5 N.

15. The cleansing composition according to claim 1, wherein the cleansing composition is characterized as providing a foaming profile in a range from about 90 mm to greater than 100 mm.

16. The cleansing composition according to claim 15, wherein the cleansing composition foaming profile is obtained with a composition at a 10× dilution after 15 seconds of agitation at a speed of about 8000 rpm.

17. A cleansing composition, comprising:
   i. at least one polysaccharide derivative selected from the group consisting of holosides, non-sulfated glycosaminoglycans, and combinations thereof;
   ii. a blend of two or more surfactants consisting essentially of two or more anionic surfactants, two or more amphoteric surfactants, or at least one anionic surfactant and at least one amphoteric surfactant, and
   iii. at least one humectant present in the cleansing composition in an amount from 1% to 15%, by weight, based on the weight of the cleansing composition,
      wherein the cleansing composition is free of cationic polymers comprising Polyquaternium-10, free of amidoalkyl betaines, and free of fatty acyl sarcosinates,
   wherein the cleansing composition has a low-frictional property exhibiting a coefficient of friction from about 0.20 up to about 0.35,
   wherein the cleansing composition is free of fatty oil compounds, and
   wherein the cleansing compositions if free of fatty acid salts.

18. The cleansing composition according to claim 17, the composition further comprising:
   iii. one or more thickeners for a water-based system;
   iv. one or more humectants; and
   v. water present in an amount from at least about 75% by weight, based on the weight of the cleansing composition.

19. The cleansing composition according to claim 1, wherein the blend of two or more surfactants consists of the two or more anionic surfactants, the two or more amphoteric surfactants, or the at least one anionic surfactant and the at least one amphoteric surfactant.

20. A cleansing composition, comprising:
   i. at least one polysaccharide derivative selected from the group consisting of holosides, non-sulfated glycosaminoglycans, and combinations thereof, the at least one polysaccharide derivative present in the cleansing composition in an amount from about 0.04% to about 2%, by weight, based on the weight of the cleansing composition;
   ii. a blend of two or more surfactants consisting essentially of two or more anionic surfactants, two or more amphoteric surfactants, or at least one anionic surfactant and at least one amphoteric surfactant, the blend of two or more surfactants being present in the cleansing composition in an amount from about 4% to about 12%, by weight, based on the weight of the cleansing composition; and
   iii. at least one humectant present in the cleansing composition in an amount from 1% to 15%, by weight, based on the weight of the cleansing composition, wherein the cleansing composition is free of fatty oil compounds and the cleansing composition has a low-frictional property exhibiting a coefficient of friction from about 0.20 up to about 0.35.

* * * * *